United States Patent [19]

Szczepanski

[11] Patent Number: 4,670,559

[45] Date of Patent: Jun. 2, 1987

[54] 2-AMINO-4-CYCLOPROPYL-1,3,5-TRIAZINES AS INTERMEDIATES FOR THE PRODUCTION OF HERBICIDALLY ACTIVE N-(CYCLOPROPYL-TRIAZINYL)-N'-ARYL-SULFONYL UREAS

[75] Inventor: Henry Szczepanski, Wallbach, Switzerland

[73] Assignee: Ciba-Geigy Corporation, Ardsley, N.Y.

[21] Appl. No.: 821,174

[22] Filed: Jan. 21, 1986

Related U.S. Application Data

[60] Continuation-in-part of Ser. No. 693,641, Jan. 22, 1985, abandoned, which is a division of Ser. No. 535,527, Sep. 26, 1983, Pat. No. 4,515,626.

[30] Foreign Application Priority Data

Oct. 6, 1982 [CH] Switzerland ............... 5874/82

[51] Int. Cl.$^4$ ............... C07D 251/18; C07D 251/42; C07D 251/16
[52] U.S. Cl. ............................. 544/211; 544/216
[58] Field of Search ............................. 544/211

[56] References Cited

U.S. PATENT DOCUMENTS 3,270,015 8/1966 Ursprung ............... 544/113

FOREIGN PATENT DOCUMENTS 1094858 12/1967 United Kingdom ............... 544/194

OTHER PUBLICATIONS

Kabbe et al., Liebigs Ann. Chem. 704, 1967, pp. 140–143.

Primary Examiner—John M. Ford
Assistant Examiner—J. G. Mullins
Attorney, Agent, or Firm—Edward McC. Roberts; Kevin T. Mansfield

[57] ABSTRACT

2-Amino-4-cyclopropyl-1,3,5-triazines and processes for their production are disclosed. The 2-amino-4-cyclopropyl-1,3,5-triazines are intermediate in the production of herbicidally active N-(cyclopropyltriazinyl)-N'-arylsulfonyl ureas and correspond to the formula

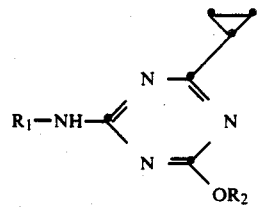

wherein $R_1$ is hydrogen, $C_1$–$C_4$-alkyl or $C_1$–$C_4$-alkoxy, and $R_2$ is $C_1$–$C_3$-alkyl, $C_1$–$C_3$-haloalkyl or $C_2$–$C_6$-alkoxyalkyl.

3 Claims, No Drawings

2-AMINO-4-CYCLOPROPYL-1,3,5-TRIAZINES AS INTERMEDIATES FOR THE PRODUCTION OF HERBICIDALLY ACTIVE N-(CYCLOPROPYL-TRIAZINYL)-N'-ARYLSULFONYL UREAS

This is a continuation-in-part of my copending application, Ser. No. 693,641, filed Jan. 22, 1985, now abandoned, which in turn is a divisional of my application Ser. No. 535,527, filed Sept. 26, 1983, now U.S. Pat. No. 4,515,626.

The present invention relates to 2-amino-4-cyclopropyl-1,3,5-triazines and a proces for their production. The 2-amino-4-cyclopropyl-1,3,5-triazines are intermediates in the production of herbicidally active N-(cyclopropyl-triazinyl)-N'-arylsulfonyl ureas. They correspond to the formula I

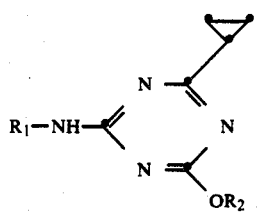

wherein
$R_1$ is hydrogen, $C_1$–$C_4$-alkyl or $C_1$–$C_4$-alkoxy and
$R_2$ is $C_1$–$C_3$-alkyl, $C_1$–$C_3$-haloalkyl or $C_2$–$C_6$-alkoxyalkyl.

Some 2-amino-4-cyclopropyl-1,3,5-triazines are known see e.g. 2-amino-4,6-dicyclopropyl-1,3,5-triazine in Ann 70 (1067) p. 140–143 or UK-patent No. 1 043 858, compound 12. 4-Amino-2-diallylamino-6-cyclopropylamino in U.S. Pat. No. 3 270 015, example 27.

The 2-Amino-4-cyclopropyl-triazines of formula I are new and produced by reacting a 2-amino-4-cyclopropyl-6-trichloromethyl-1,3,5-triazine of the formula II

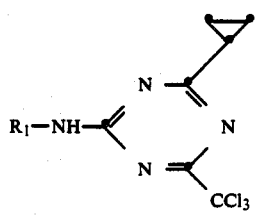

wherein $R_1$ is hydrogen, $C_1$–$C_4$-alkyl or $C_1$–$C_4$-alkoxy, in an anhydrous organic solvent, with at least the molar amount of an alkanol of the formula III or an alkali metal salt thereof, $R_2OH$ (III)

wherein $R_2$ is $C_1$–$C_3$-alkyl, $C_1$–$C_3$-haloalkyl or $C_2$–$C_6$-alkoxyalkyl.

The 2-amino-4-cyclopropyl-triazines of formula I can also be prepared by reaction of 4-cyclopropyl-2,6-bis-trichloromethyl-1,3,5-triazine of formula IV

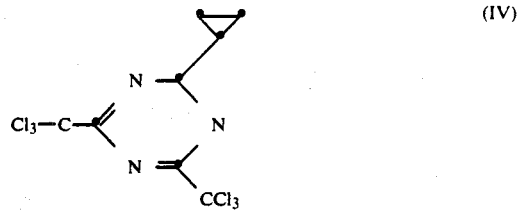

in an anhydrous organic solvent, with at least the twice molar amount of an alkanol of formula III or an alkali metal salt thereof, $R_2OH$ (III)

wherein $R_2$ is $C_1$–$C_3$-alkyl, $C_1$–$C_3$-haloalkyl or $C_2$–$C_6$-alkoxyalkyl and converting the 2-cyclopropyl-4,6-bis-alkoxy-1,3,5-triazine obtained at a higher temperature of 40°–140° C. and under pressure with at least the molar amount of an amine of the formula V $HNR_1$ (V)

wherein $R_1$ is hydrogen, $C_1$–$C_4$-alkyl or $C_1$–$C_4$-alkoxy.

In order to obtain herbicidally active N-(cyclopropyl-triazinyl)-N'-arylsulfonyl ureas, the 2-amino-4-cyclopropyl-1,3,5-triazines of formula I obtained can be reacted directly with an arylsulfonylisocyanate, or they can be converted by reaction in a known manner into an isocyanate or into a carbamic acid ester.

2-Amino-4-cyclopropyl-6-trichloromethyl-1,3,5-triazine is produced by condensing 2 moles of trichloroacetonitrile with one mole of cyclopropylnitrile in the presence of hydrogen chloride to give 4-cyclopropyl-2,6-bis-(trichloromethyl)-1,3,5-triazine, and then reacting this compound with one mol of ammonia or of an amine at temperatures of −20°–160° C. under normal pressure, corresponding to the reaction scheme:

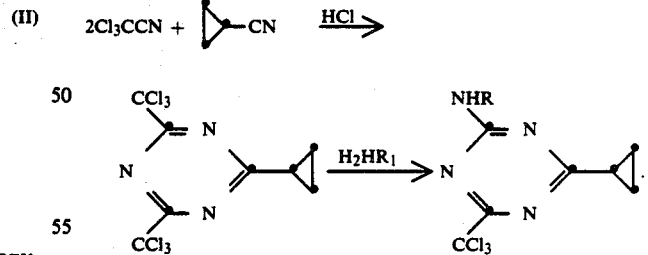

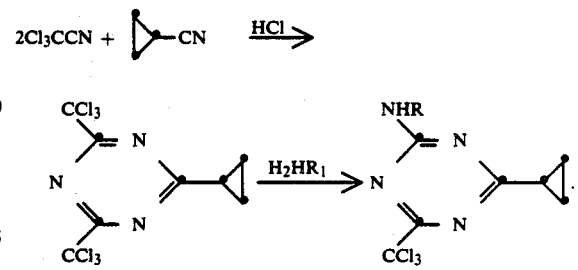

The 2-amino-4-cyclopropyl-triazines of formula I can also be prepared, starting from a 2-(γ-chloropropyl)4,6-bis-(trichloromethyl)-1,3,5-triazine, which is obtained by condensation of 2 moles of trichloroacetonitrile and one mol of γ-chlorobutyronitrile in the presence of hydrogen chloride.

2 $Cl_3CCN$ + $ClCH_2CH_2CH_2CN$ ⟶

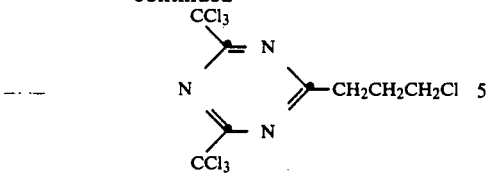

This compound can be reacted with the molar amount of amine H₂NR₁ at −20°–60° C. under normal pressure to give 2-amino-4-(γ-chloropropyl)-6-trichloromethyl-1,3,5-triazine, which is converted with an alkalimetal alcoholate R₂O⊖M⊕ in an organic solvent at 0°–200° C. into 2-amino-4-cyclopropyl-6-alkoxy-1,3,5-triazine.

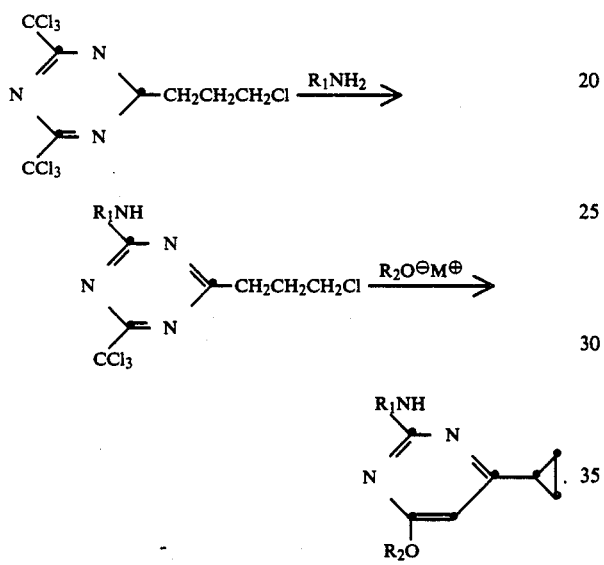

The process is characterized by reacting 2-(γ-chloropropyl)-4,6-bis-trichloromethyl-1,3,5-triazine in an inert solvent at 0°–160° C. under normal pressure with the molar amount of an amine of the formula IV

wherein R₁ has the above given meaning, and converting the 2-amino-4-(γ-chloropropyl)-6-trichloromethyl-1,3,5-triazine obtained in an organic solvent at −20°–200° C. with two moles of an alkali-metal alcoholate of the formula IIIa

wherein M⊕ is an alkali-metal cation and R₂ has the above-given meaning.

These reactions are advantageously performed in aprotic, inert organic solvents, such as methylene chloride, tetrahydrofuran, acetonitrile, dioxane and toluene or in lower alkanols.

The reaction temperatures are preferably between −20° and +120° C. The reactions proceed in general slightly exothermically, and can be performed at room temperature. For the purpose of shortening the reaction time or of initiating the reaction, heat is advantageously applied for a short time up to the boiling point of the reaction mixture.

The final products can be isolated by concentration and/or by evaporating off the solvent, and purified by recrystallisation or by trituration of the solid residue in solvents in which they do not readily dissolve, such as ethers, aromatic hydrocarbons or chlorinated hydrocarbons.

In the following Examples which explain the invention in more detail, the temperatures are given in degreed Centigrade (°C.), and pressures in millibars (mb).

EXAMPLE 1

Production of 2-cyclopropyl-4,6-bis-trichloromethyl-1,3,5-triazine (intermediate)

760 g of trichloroacetonitrile are cooled to −15° C., and hydrogen chloride gas is blown through the solution until saturation is attained. There are then slowly added, with cooling and introduction of hydrogen chloride gas, 230 g of cyclopropylnitrile in such a manner that the temperature does not exceed −10° C. The cooling bath is subsequently removed and the reaction mixture is stirred at room temperature until the temperature rises to 15° C. There commences from 10° C. upwards, with a moderately exothermic reaction, the splitting-off of hydrogen chloride which, after 20 hours' stirring at 15°–20° C., has finished.

1.5 liters each of ether and hexane are added to the reaction mixture; the whole is then thoroughly stirred and afterwards filtered. The filtrate is concentrated by evaporation; the residue is boiled up in 700 ml of hexane, filtration is again performed and the filtrate is once more concentrated by evaporation. The residue is recrystallised from methanol to thus obtain 350 g of the above triazine, m.p. 100°–102° C.

EXAMPLE 2

Production of 2-amino-4-cyclopropyl-6-trichloromethyl-1,3,5-triazine 71.2 g of 2-cyclopropyl-4,6-bis-trichloromethyl-1,3,5-triazine are dissolved in 70 ml of tetrahydrofuran, and at room temperature are added, with stirring, 300 ml of a concentrated aqueous ammonia solution. The reaction mixture is stirred for 30 minutes; it is then diluted with water, and the formed emulsion is extracted with ether. The ether phases are collected, dried, filtered and subsequently concentrated by evaporation. The residue crystallises and there remain 48 g of the crystalline title product, m.p. 111°–114° C.

EXAMPLE 3

Production of 2-cyclopropyl-4-methoxy-6-trichloromethyl-1,3,5-triazine

To a solution of 48 g of 2-cyclopropyl-4,6-bis-(trichloromethyl)-1,3,5-triazine in 200 ml of MeOH are added, with stirring, 4.9 g of sodium methylate, and the mixture is stirred for 1 hour at room temperature; it is then filtered and the filtrate is evaporated to dryness. The yield is 28.5 g of the title compound as a light-red oil, which solidifies after some time, m.p. 49°–51° C.

EXAMPLE 4

Production of 2-cyclopropyl-4,6-dimethoxy-1,3,5-triazine (intermediate)

8.1 g of sodium methylate are added to a solution of 71.2 g of 2-cyclopropyl-4,6-bis-(trichloromethyl)-1,3,5- triazine in 200 ml of methanol, and stirring is maintained for 5 hours at room temperature. The solution is then evaporated to dryness, and the residue is stirred up with 200 ml of ether. The resulting suspension is filtered and the filtrate is concentrated by evaporation. The residue crystallises, and is recrystallised from ether/hexane. The yield is 35.7 g of the above triazine, m.p. 68°–70° C.

EXAMPLE 5

Production of 2-cyclopropyl-4-amino-6-methoxy-1,3,5-triazine

To a solution of 10.8 g of sodium methylate in 50 ml of methanol are added 28.9 g of 2-amino-4-(3-chloropropyl)-6-trichloromethyl-1,3,5-triazine, and the mixture is stirred at 60° C. for 80 minutes. The formed suspension is filtered under suction, diluted with 250 ml of water, and extracted 3 times with 200 ml of ethylene chloride each time. The organic phases are dried, filtered, and concentrated by evaporation. The oil which remains in purified through a silica gel column, the eluant is evaporated off to leave 2.1 g of the title product, which is recrystallised from ether/chloroform, m.p. 158°–159° C.

EXAMPLE 6

Production of 2-amino-4-cyclopropyl-6-methoxy-1,3,5-triazine

Gaseous ammonia is blown through a solution of 5 g of 2-cyclopropyl-4,6-dimethoxy-1,3,5-triazine in 30 ml of methanol at room temperature until saturation is reached. The solution is then stirred in a bomb tube (autoclave) at 140° C. for 1 hour; it is subsequently cooled, and the reaction mixture is filtered to thus obtain 0.5 g of the title product as light-brown crystals, m.p. 156°–157° C.

EXAMPLE 7

Production of 2-amino-4-cyclopropyl-6-methoxy-1,3,5-triazine 5 ml of concentrated aqueous ammonia are added to a solution of 1 g of 2-cyclopropyl-4-methoxy-6-trichloromethyl-1,3,5-triazine in 3 ml of tetrahydrofuran; the whole is placed into a bomb tube and heated at 80° C. for 30 minutes. The mixture is cooled and then filtered; the filter residue is dissolved in 30 ml of methylene chloride, and the solution is dried over magnesium sulfate, and concentrated by evaporation. The residue crystallises to leave 0.4 g of white crystals, m.p. 157°–158° C.

EXAMPLE 8

Production of 2-amino-4-(3-chloropropyl)-6-trichloromethyl-1,3,5-triazine (intermediate)

102.3 g of 2-(3-chloropropyl)-4,6-bis-(trichloromethyl)-1,3,5-triazine are dissolved in 100 ml of tetrahydrofuran, and to this solution are added, whilst it is being stirred at room temperature, 400 ml of concentrated aqueous ammonia solution. After 30 minutes are added 500 ml of water, and the reaction mixture is extracted twice with 100 ml of ether each time. The ether phases are dried over magnesium sulfate, filtered, and concentrated by evaporation to yiled 68.3 g of the title product as light-brown oil.

EXAMPLE 9

Production of 2-(3-chloropropyl)-4,6-bis-(trichloromethyl)-1,3,5-triazine (intermediate)

Gaseous hydrogen chloride is blown through a solution of 103 g of 4-chlorobutyronitrile in 298 g of trichloroacetonitrile at a temperature of −20° C. until saturation is reached. The mixture is then slowly warmed to room temperature with stirring, in the course of which only a relatively small evolution of gas results and a crystalline precipitate occurs. One liter of toluene is added and the reaction mixture is stirred at 85° C. until no further HCl gas evolves. Stirring is then ceased and the mixture is allowed to cool; the clear solution is decanted from the sludge which has settled. The solution is concentrated by evaporation, and the oil remaining is distilled under high vacuum to thus obtain 294 g of the title compound; b.p. 150°–160° C./0.2 mbar; refractive index $n_D^{27}$:1.5498.

EXAMPLE 10

Production of 2-amino-4-cyclopropyl-6-methoxy-1,3,5-triazine 25.3 g of 2-amino-4-cyclopropyl-6-trichloromethyl-1,3,5-triazine are added to a solution of 10.8 g of sodium methylate in 50 ml of methanol, and the mixture is stirred at 60° C. for 80 minutes. There are added 300 ml of water, and the formed suspension is filtered. The filter residue is suspended twice in 100 ml of acetyl acetate each time, and again filtered. The organic phases are collected, dried over magnesium sulfate and concentrated by evaporation to thus obtain an oil, which crystallises when stirred up in ether. The yield is 6.7 g of the title compound, m.p. 158°–159° C.

In a manner analogous to that of these Examples, there are produced the following triazines.

| Q | X | Y | Physical data | |
|---|---|---|---|---|
| CCl$_3$ | cyclopropyl | CCl$_3$ | m.p. 100–102° C. | Ex. 1 |
| NH$_2$ | cyclopropyl | CCl$_3$ | m.p. 114–116° C. | Ex. 2 |
| OCH$_3$ | cyclopropyl | CCl$_3$ | m.p. 49–51° C. | Ex. 3 |
| OCH$_3$ | cyclopropyl | OCH$_3$ | m.p. 68–70° C. | Ex. 4 |
| NH$_2$ | cyclopropyl | OCH$_3$ | m.p. 158–159° C. | Ex. 5, 6, 7, 10 |
| NH$_2$ | Cl C$_3$H$_6$— | CCl$_3$ | oil | Ex. 8 |
| CCl$_3$ | Cl C$_3$H$_6$— | CCl$_3$ | oil $n_D^{27}$: 1.5498 | Ex.9 |
| NHC$_3$H$_{7n}$ | cyclopropyl | CCl$_3$ | oil | |
| NHC$_3$H$_{7n}$ | cyclopropyl | NHC$_2$H$_5$ | oil | |
| OCH$_3$ | cyclopropyl | OH | m.p. 160–164° C. | |
| NHC$_3$H$_{7n}$ | cyclopropyl | NH$_2$ | resin | |
| OC$_2$H$_5$ | cyclopropyl | CCl$_3$ | oil | |
| NHCH$_3$ | cyclopropyl | CCl$_3$ | m.p. 100–102° C. | |
| NHC$_2$H$_5$ | cyclopropyl | CCl$_3$ | m.p. 47–49° C. | |

-continued

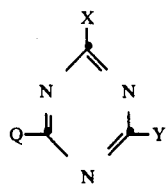

| Q | X | Y | Physical data |
|---|---|---|---|
| NHC$_3$H$_7$iso | cyclopropyl | CCl$_3$ | oil |
| N(CH$_3$)$_2$ | cyclopropyl | CCl$_3$ | m.p. 59–61° C. |
| NHCH$_3$ | cyclopropyl | OCH$_3$ | |
| NHCH$_3$ | cyclopropyl | OC$_2$H$_5$ | |
| NHCH$_3$ | cyclopropyl | OCH$_2$CF$_3$ | |
| NH$_2$ | cyclopropyl | OC$_2$H$_5$ | |
| NH$_2$ | cyclopropyl | OCH$_2$CF$_3$ | |
| NH$_2$ | cyclopropyl | OC$_2$H$_4$Cl | |
| NH$_2$ | cyclopropyl | OC$_2$H$_4$OCH$_3$ | |
| NH$_2$ | cyclopropyl | OCH(CH$_3$)$_2$ | |
| NH$_2$ | cyclopropyl | SCH$_3$ | |
| NH$_2$ | cyclopropyl | NHNHCH$_3$ | |
| NH$_2$ | cyclopropyl | N(CH$_3$)NHCH$_3$ | |
| NH$_2$ | cyclopropyl | NHCOCH$_3$ | |

-continued

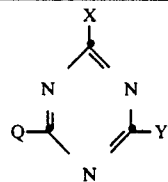

| Q | X | Y | Physical data |
|---|---|---|---|
| NH$_2$ | cyclopropyl | NH$_2$ | |

What is claimed is:

1. A 2-amino-4-cyclopropyl-1,3,5-triazine of the formula

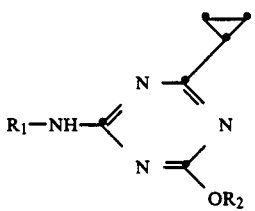

wherein
R$_1$ is hydrogen, C$_1$–C$_4$-alkyl or C$_1$–C$_4$-alkoxy and
R$_2$ is C$_1$–C$_3$-alkyl, C$_1$–C$_3$-haloalkyl or C$_2$–C$_6$-alkoxyalkyl.

2. 2-Amino-4-cyclopropyl-6-methoxy-1,3,5-triazine according to claim 1.

3. 2-Amino-4-cyclopropyl-6-ethoxy-1,3,5-triazine according to claim 1.

* * * * *